(12) United States Patent
Schulze-Forster et al.

(10) Patent No.: US 8,592,164 B2
(45) Date of Patent: Nov. 26, 2013

(54) METHOD FOR DIAGNOSIS OF A DISEASE INVOLVING AN ANTI-ENDOTHELIN-RECEPTOR ANTIBODY

(75) Inventors: Kai Schulze-Forster, Teltow (DE); Harald Heidecke, Berlin (DE)

(73) Assignee: CellTrend GmbH, Luckenwalde (DE)

( * ) Notice: Subject to any disclaimer, the term of this patent is extended or adjusted under 35 U.S.C. 154(b) by 674 days.

(21) Appl. No.: 12/376,200

(22) PCT Filed: Jul. 31, 2007

(86) PCT No.: PCT/EP2007/057911
§ 371 (c)(1), (2), (4) Date: Sep. 30, 2009

(87) PCT Pub. No.: WO2008/015219
PCT Pub. Date: Feb. 7, 2008

(65) Prior Publication Data
US 2010/0075348 A1 Mar. 25, 2010

(30) Foreign Application Priority Data
Aug. 4, 2006 (EP) .................................. 06016297

(51) Int. Cl.
G01N 33/00 (2006.01)
G01N 33/48 (2006.01)
G01N 33/487 (2006.01)
G01N 33/50 (2006.01)
G01N 33/53 (2006.01)

(52) U.S. Cl.
USPC .......... 435/7.1; 435/7.23; 514/16.6; 514/15.7

(58) Field of Classification Search
None
See application file for complete search history.

(56) References Cited

U.S. PATENT DOCUMENTS

| 7,745,139 B1 | 6/2010 | Wallukat et al. |
| 2004/0192634 A1 | 9/2004 | Schulze-Forster et al. |
| 2005/0014200 A1 | 1/2005 | MacVicar |
| 2006/0263835 A1* | 11/2006 | Wallukat ..................... 435/7.92 |
| 2010/0098688 A1 | 4/2010 | Schulze-Forster |

FOREIGN PATENT DOCUMENTS

| EP | 0480381 A | 4/1992 |
| EP | 2007057911 R | 11/2007 |
| WO | WO0037075 | 6/2000 |
| WO | WO 00/39154 | 7/2000 |
| WO | WO 02/10753 | 2/2002 |
| WO | WO 02/093171 | 11/2002 |
| WO | WO 2004/051280 A2 * | 6/2004 |
| WO | WO 2006/060336 | 6/2006 |
| WO | PCT/EP2007/057911 R | 11/2007 |
| WO | WO2008015218 | 5/2008 |

OTHER PUBLICATIONS

Perez (2005, Ann. N.Y. Acad. Sci. 1062:155-164).*
Benigni, Ariela and Giuseppe Remuzzi. "Endothelin Antagonists." The Lancet vol. 353, (Jan. 9, 1999): 133-138.
McLaughlin, V. V. "Pulmonary Arterial Hypertension: Current Diagnosis and Management." (ACC Current Journal Review), May/Jun. 2002, 17-21, 11:3.
Morris, C.D. et al. "Specific inhibition of the endothelin a receptor with ZD4054: clinical and pre-clinical evidence." (British Journal of Cancer), Jun. 2005, 2148-2152, 92:12.
O'Callaghan, D. S. et al. "Sitaxsentan: an endothelin—A receptor antagonist for the treatment of pulmonary arterial hypertension." (International Journal of Clinical Practice), Apr. 2006, 475-481, 60:4.
Plan. "Acquisitions recentes en rhumatologie." (Medecine & Hygiene), Oct. 2, 2002, 1803-1808, 60:2407.
Plan. "Acquisitions recentes en rhumatologie." (Medecine & Hygiene), Oct. 2, 2002, 1803-1808, 60:2407. (English Translation).
Suzuki, N., et al. "A Sensitive Sandwich-Enzyme Immunoassay for Human Endothelin." Journal of Immunological Methods, 1989: vol. 118, 245-250.
Charles Haas, "Pulmonary Hypertension Associated With Systemic Lupus Erythematosus", Bulletin of the National Academy of Medicine, Netherlands, 2004, vol. 188, No. 6, pp. 985-997, Medline/NLM English Abstract 1 page (XP-002415918).
Ortmann J., et al.: "Endothelin inhibition delays onset of hyperglycemia and associated vascular injury in type 1 Diabetes: Evidence for endothelin release by pancreatic islet β-cells", Biochem. Biophys. Res. Comm., vol. 334, 2005, pp. 689-695.
Schiffrin E. L.: "Vascular endothelin in hypertension", Vascular Pharmacol., vol. 43, 2005, pp. 19-29.
Amman K., et al: "Blood Pressure-Independent Additive Effects of Pharmacologic Blockade of the Renin-Angiotensin and Endothelin Systems on Progression in a Low-Renin Model of Renal Damage", J. Am. Soc. Neprol., vol. 12, 2001, pp. 2571-2584.
Dragun D., et al: "Angiotensin II type 1-receptor activating antibodies in renal-allograft rejection", Feb. 10, 2005, New England journal of Medicine, vol. 352, NR. 6, pp. 558-569.
Thway T. M., et al.: "Antibodies from preeclamptic patients stimulate increased intracellular Ca2+ mobilization through angiotensin receptor activation", Sep. 21, 2004, Circulation, vol. 110, NR. 12, pp. 1612-1619.
Walsh D. A., et al.: "AT receptor characteristics of angiotensin analogue binding in human synovium", British Journal of Pharmacology, Basingstoke, Hants, GB, vol. 112, No. 2, Jun. 1, 1994, pp, 435-442.

(Continued)

*Primary Examiner* — Elizabeth C Kemmerer
(74) *Attorney, Agent, or Firm* — Parker Highlander PLLC (57) ABSTRACT

The invention relates to a method for diagnosis of a disease, wherein presence or absence of an anti-endothelin-receptor antibody is determined in a sample from a patient to be diagnosed more in particular an anti-endothelin-receptor-A antibody. The disease according to the invention is in particular selected from diabetes, preferably type I diabetes, graft rejection, pre-eclampsia, hypertension, vasculitis, collagenosis, Raynaud-Syndrom (Morbus Raynaud), and inflammatory rheumatic disease and arteriosclerosis. The invention further relates to the use of an inhibitor of an anti-endothelin-receptor antibody or an inhibitor of an endothelin-receptor for the production of a medicament as well as a method for removing anti-endothelin-receptor antibodies from isolated blood by means of plasmapheresis.

9 Claims, 4 Drawing Sheets

(56) References Cited

OTHER PUBLICATIONS

Dalbeth N., et al: "The non-thiol angiotensin-converting enzyme inhibitor quinapril suppresses inflammatory arthritis", Rheumatology, Oxford University Press, London, GB, vol. 44, No. 1, Jan. 2005, pp. 24-31.

Cheng Zhong Jian, et al: "Angiotensin II and vascular inflammation.", Medical Science Monitor: International Medical Journal of Experimental and Clinical Research Jun. 2005, vol. 11, No. 6, Jun. 2005, pp. RA194-RA205.

Ruiz-Ortega M., et al: "Proinflammatory actions of angiotensins", Current Opinion in Nephrology and Hypertension, May 1, 2001, pp. 321-329.

Gohji K., et al: "Expression of endothelin receptor A associated with prostate cancer progression", Journal of Urology, Baltimore, MD, US, vol. 165, No. 3, Mar. 2001, pp. 1033-1036.

Cobankara, et al., "Renin and Angiotensin-Converling Enzyme (ACE) as Active Components of the Local Synovial Renin-Angiotensin System in Rheumatoid Arthritis", Rheumatology International, vol. 25, No. 4, (May 1, 2005) 285-291.

Pitotti, et al., "HPLC method for evaluation of urinary angiotensin-converting enzyme: some examples of normal subjects and patients with renal transplantation". Journal of Pharmaceutical and Biomedical Analysis, vol. 4, No. 5, 677-683, 1986.

Colonna, et al., "Non-Renin Dependent Hypertension in Renal Aliograft Rejections. A structural and functional analysis", Archives of Pathology & Laboratory Medicine, vol. 108, No. 2, 117-120, Feb. 1984.

Oldfield, et al., "Efferent Neural Projections of Angiotensin Receptor (AT1) Expressing Neurons in the Hypothalamic Paraventricular Nucleus of the Rat", Journal of Neuroedocrinology, vol. 13, No. 2, 139-146, 2001.

Inigo, et al., "Effects of losartan and aminodipine on intrarenal hemodynamics and TGT-beta 1 plasma levels in a crossover trial in renal transplant recelpients", Journal of the American Society of Nephroiogy, vol. 12, 822-827, 2001.

Fu, et al., "Autoantibodies against the angiotensin receptor (AT1) in patients with hypertension", Journal of Hypertension, vol. 18, 945-953, 2000.

Dechend, et al., "AT1 receptor agonistic antibodies from preeclamptic patients cause vascular cells to express tissue factor", Circulation, vol. 101, 2382-2387, 2000.

Bachy, et al., "Hypertension after renal transplantation" British Medical Journal, vol. 2, 1287-1289, 1976.

Wallukat, et al., "Patients with preeclampsia develop agonistic auto antibodies against the angiotensin AT1receptor", J. Clin. Investig., 103, 945-952, 1999.

Liao, et al, "Auto antibodies against AT1-Receptor and a1-AdrenergicReceptor in Patients with Hypertension", Hypertension Res., 25, 641-646, 2002.

Restriction Requirement, dated Jul. 30, 2010. issued in U.S. Appl. No. 12/376,164, 8 pages.

Non-Final Office Action, dated Oct. 13, 2010. issued in U.S. Appl. No. 12/376,164, 7 pages.

Non-Final Office Action, dated Apr. 21, 2011, Issued in U.S. Appl. No. 12/376,164. 13 pages.

Final Office Action, dated Oct. 28. 2011, issued in U.S. Appl. No. 12/376,164, 9 pages.

* cited by examiner

METHOD FOR DIAGNOSIS OF A DISEASE INVOLVING AN ANTI-ENDOTHELIN-RECEPTOR ANTIBODY

The instant application contains a Sequence Listing which has been submitted via EFS-Web and is hereby incorporated by reference in its entirety. Said ASCII copy, created on Dec. 10, 2012, is named 0054_0010_US1_Sequence_Listing.txt and is 586 bytes in size.

The present invention is in the filed of biology, chemistry more in particular immunology as well as diagnostics and therapeutics, more in particular in the field of the diagnosis of graft rejection, pre-eclampsia, also referred to as toxemia, hypertension, vasculitis, collagenosis and inflammatory rheumatic disease as well as arteriosclerosis.

For successful organ transplantation, the donor organ is required to mach histologically with the tissue of the recipient as much as possible. Such matching is determined via the HLA-System (human leukocyte antigen), which is a complex system of tissue antigens occurring on virtually any cell. Said system plays an important physiological role in immunological defense reactions (recognition of "self" and "non-self"). Prior to each transplantation, therefore, a so called tissue typing is effected in the organ donor and recipient so as to ensure HLA-completability as much as possible.

As a result of the immense genetic polymorphism there is an exceptionally large number of various HLA-molecules. Complete match solely is observed in monozygotic twins. Otherwise, HLA-molecules are unique to each person.

However, problems exist in that rejection reactions against the transplanted organ cannot be ruled out despite extensive HLA match between recipient and donor.

WO 02/093171 discloses an invention which relates to the use of AT' or functionally analogous peptides or proteins thereof in order to predict (diagnose) the risk of transplant rejection.

Still there is a need to provide an efficient and reliable method allowing positive and rapid predictability as to the risk of transplant rejection reaction.

Pre-eclampsia (previously called toxemia) is a hypertensive disorder of pregnancy with associated protein loss in the urine. Early identification may prevent progression to the convulsions of eclampsia or multi system effects of HELLP-Syndrome that are potentially fatal to both mother and fetus.

Pre-eclampsia is difficult to diagnose. Pre-eclampsia is diagnosed when pregnant women develop high blood pressure (two separate readings taking at least six hours apart of 140/90 or more) and 300 mg of protein in a 24 hour urine sample (proteinuria), swelling or edema (especially in the hands and face) was originally considered an important sign for the diagnosis of pre-eclampsia but in current medical practice only hypertension and proteinuria are necessary for a diagnosis. Some women develop high blood pressure without the proteinuria; this is called pregnancy induced hypertension (PIH) or gestational hypertension. Both pre-eclampsia and PIH are regarded as very serious conditions and require careful monitoring of mother and baby.

Pre-eclampsia is much more common in the first pregnancy (3-5%) of births and usually becomes evident in the third trimester (and virtually always after the 20$^{th}$ week of pregnancy). It is also more common in women which have pre-existing hypertension, diabetes, autoimmune diseases like, lupus, various inherited thrombofilias, like factor V Leiden or renal diseases in women with a family history of pre-eclampsia and in women with a multiple gestation (twins, triplets, and more). Pre-eclampsia is thought to be caused by a shallowly implanted placenta which becomes hypoxic, leading to upregulated inflammatory mediators, secreted by the placenta enacting on the vascular endothelium. If severe, it progresses to fulminant pre-eclampsia, with headaches, visual disturbances and epigastric pain and further to HELLP-Syndrome in eclampsia. Placental abruption is associated with hypertensive pregnancies. These are life-threatening conditions for both the developing fetus and the mother.

Despite extensive research, the exact aethiology and pathophysiology of the condition remain unclear. It is likely, however, that inadequate placental perfusion resulting from inadequate placental invasion precipitates the release of some form of chemical trigger which, in susceptible mothers, leads to endothelial damage, metabolic changes and a form of inflammatory response.

So far the only known treatment of eclampsia for advancing pre-eclampsia is delivery. Either by induction of Caesarean Section, hypertension can sometime be controlled with anti-hypertensive medication, but any effect this might have on the progression of the underlying disease is unknown. In some cases women with pre-eclampsia or eclampsia can be stabilized temporarily with magnesium sulfate intravenously to forstall seizures while steroid shots are administered to promote fetal lung maturation. As of 2006 sildenafilcitrate (Viagra) was in phase II clinical trials for the treatment of pre-eclampsia.

Thus, there is a need for a safe and reliable diagnostic tool relating to the diagnosis of pre-eclampsia as well as a need for a medicament for the treatment of pre-eclampsia.

Hypertension or high blood pressure is a medical condition wherein the blood pressure is chronically elevated. While it is formally called arterial hypertension, the word "hypertension" without a qualifier usually refers to arterial hypertension. Persistent hypertension is one of the risk factors for strokes, heart attacks, heart failure and arterial aneurism, and is a leading cause of chronic renal failure.

Blood pressure is a continuously distributed variable, and the risk of associated cardiovascular disease likewise rises continuously. The point at which blood pressure is defined as hypertension is therefore somewhat arbitrary. Presently, finding sustained blood pressure of 140/90 mmHg or above, measured on both arms, is generally regarded as diagnostic. Because blood pressure readings in many individuals are highly variable—especially in the office setting—the diagnosis of hypertension should be made only after noting a mean elevation of two or more readings, one two or more office visits, unless the elevations are severe or associated with compelling indications such as diabetes mellitus, chronic kidney disease, heart failure, postmyocardial infarction, stroke and high coronary disease risk. Recently, the JNC7 (the seventh report of the Joint National Committee on prevention, detection, evaluation and treatment of high blood pressure has defined blood pressure 120/80 mmHg to 139/89 mmHg as "pre hypertension". Pre-hypertension is not a disease category; rather it is a designation chosen to identify individuals at high risk of developing hypertension. Due to the fact that diagnosis of hypertension is difficult, there is a need for a further tool for diagnosing hypertension. Also, there is a need for a medicament for the treatment of hypertension.

In medicine, vasculitis (plural: vasculitides) is a group of diseases featuring inflammation of the wall of blood vessels due to leukocyte migration and resulting damage. While most vasculitides are rare, they generally effect several organ systems and can cause severe disability. Vasculitides are classified into the large vessel vasculitis such as Takayasu arteritis and giant cell (temporal) arteritis. Further, medium vessel vasculitis, such as polyarteritis nodosa and Kawasaki disease.

Small vessel vasculitis such as Churg-Strauss arteritis, Wegener's granulomatosis and hypersensitivity vasculitis.

Patients usually present with systemic symptoms with single or multi organ dysfunction. Common (and nonspecific) complaints include fatigue, weakness, fever, arthralgias, abdominal pain, hypertension, renal insufficiency, a neurologic dysfunction. The following symptoms should raise a strong suspicion of vasculitis, however, the diagnosis is difficult. These symptoms are monoeuritis multiplex, palpable purpura and pulmonary-renal.

A detailed history is important to elicit any recent medications, any risk of hepatitis infection or any recent diagnosis with a connective tissue disorder such as SLE. Diagnosis may include an antinuclear antibody (ANA) test which detects an underlying connectivity tissue disorder, especially SLE. Diagnosis may also include antineutrophil cytoplasmic antibody (ANCA) which may suggest Wegener's granulomatosis, polyarteritis nodosa, Chrug-Strauss-Syndrome or drug-induced vasculitis, but is not diagnostic. The only safer way of diagnosing vasculitis is a tissue biopsy which at present is the "gold standard" of diagnosis.

Thus, there is a need for a diagnostic tool for diagnosing vasculitis. Further, there is a need for a medicament for the treatment of vasculitis.

Collagenosis is the term for a group of rare autoimmune diseases. Here the body creates antibodies against parts of the connective tissue. Collagenosis are diseases such as SLE, systemic lupus, Wegener granulomatosis, CREST-Syndrome and SHARP-Syndrome. Collagenosis is difficult to diagnose. Thus, there is a need for a tool for diagnosis collagenosis.

Approximately 100 million people in Europe suffer from some form of inflammatory or degenerative rheumatic disease causing the impact of rheumatic diseases on European societies to be overwhelming for society. Joint diseases account for half of all chronic conditions in persons aged 65 and over.

The quality of life of approximately 7.5% of the European population is severely and permanently reduced by pain and functional impairment caused by rheumatic diseases Immobility and reduced life expectancy are the most drastic consequences of these at present, incurable diseases. In Europe alone, rheumatic diseases impose an economic burden of more than 200 billion EUR per year. Indeed, the impact of rheumatic diseases in a social and economic burden will increase dramatically as the European population ages. A new therapy is targeting the molecules involved in the pathogenesis of chronic inflammatory disease have been developed in recent years. Despite these efforts we are still not able to cure the majority of rheumatic diseases. A therapeutic challenge includes chronicity of inflammation, autoimmunity, and degenerating muscular skeletal system. Although, rheumatic diseases differ in their immunopathology, they share common mechanisms of initiation and perpetuation. Moreover, there is a considerable translational potential for the understanding of other diseases involving the immune system, e.g. autoimmune diseases, allergy and infection. The diversity of rheumatic diseases, the multiplicity of tissues involved, i.e. bone, cartilage, joints, kidney, skin, blood vessels and the multidisciplinary approach require to understand the molecule basis of these diseases make their diagnosis very difficult.

Diagnosis of arthritis and other rheumatic diseases is often difficult, as many symptoms are similar among the different diseases. To make an accurate diagnosis, a physician may need to conduct a review of the medical history, perform a physical examination obtain laboratory tests, x-rays and other imaging tests. The rheumatic diseases are, e.g. rheumatoid arthritis, fibromyalgia, lupus erythematodes, polymyaglia rheumatica, progressive systemic sclerosis, Sjögren-Syndrome, systemic lupus ethematodes and joint inflammation.

The American College of Rheumatology has defined (1987) a number of criteria for the diagnosis of, e.g. rheumatoid arthritis. Morning stiffness of more than one hour, arthritis and soft tissue swelling of more than 3 of 14 joints/joint groups, arthritis of hand joints, symmetric arthritis, subcutaneous nodules in specific blazes, rheumatoid factor at a level above the 95 th/percentile and radiological changes suggested of joint erosion. At least four criteria have to be met to establish the diagnosis, although many patients are treated despite not meeting the criteria. When rheumatoid arthritis is being clinically suspected immunological studies are required such as rheumatoid factor (RF, a specific antibody). A negative RF does not rule out rheumatoid arthritis. Recently, a new serological test has been developed, which tests for the presence of so called anti-citrullinated protein (ACP) antibodies. Like RF, this test can detect approximately 80% of all RA patients, but is rarely positive in non-RA patients. Also, several other blood tests are usually done to allow for other causes of arthritis, such as lupus erythematosis. Such tests include the erythrocyte sedimentation rate (ESR), c-reactive protein, full-blood count, renal function, liver enzymes and immunological tests, e.g. antinuclear antibody/ANA are all performed at this stage.

As outlined for rheumatoid arthritis as one disease amongst those in the family of inflammatory rheumatic diseases, diagnosis in the field of diseases is difficult. Thus, there is a need for a safe and reliable diagnostic tool.

Artheriosclerosis is a disease affecting the arterial blood vessel. It is caused by the formation of multiple plagues within the artery.

Areas of severe narrowing, stenosis, detectable by angiography, and to a least extend "stress testing" have long been the focus of human diagnostic techniques for cardiovascular disease in general. However, these methods focus on detecting only severe narrowing, not the underlying arteriosclerosis disease. As demonstrated by human clinical studies, most severe events occur in locations with heavy plague, yet little or no lumen narrowing present before debilitating events suddenly occur. Plaque rupture can lead to artery lumen occlusion within seconds to minutes and potential permanent debility and sometimes sudden death. 77% lumen stenosis used to be considered by cardiologists as the hallmark of clinically significant disease because it is only at this severity of narrowing of the larger heart arteries that recurring episodes of angina and detectable abnormalities by stress testing methods are seen. However, clinical trials have shown that only about 14% of clinically debilitating events occur at locations with this, or greater severity of narrowing. The majority of events occur due to artheroma plague rupture at areas without narrowing sufficient enough to produce any angina or stress test abnormalities. Thus, there is an extreme need for a diagnostic method for diagnosing arteriosclerosis. Various different kinds of arteriosclerosis exist. Arteriosclerosis, such as coronary arteriosclerosis, cerebral arteriosclerosis such as apoplexy and enzephalo malacia, diabetic nephrosclerosis and juvenile malign nephrosclerosis and Mönckeberg-Arteriosclerosis.

The present invention addresses the need for a diagnostic tool for the above-mentioned family of diseases. The present invention further addresses the need for a medicament for treating the above-mentioned diseases.

SUMMARY OF THE INVENTION

The present invention relates to a method for diagnosis of a disease, wherein, presence or absence of anti-endothelinreceptor antibody is determined in a sample from a patient to be diagnosed. The presence of an anti-endothelin-receptor antibody is indicative for the disease. In a preferred embodiment of the invention the anti-endothelin-receptor antibody is an anti-endothelin-receptor-A antibody. In a preferred embodiment of the invention the disease is selected from the group of diabetes, graft rejection, pre-eclampsia also referred to as toxemia, hypertension, vasculitis, collagenosis and inflammatory rheumatic disease and arteriosclerosis.

The inventors have found that 95% of patients with graft rejection are positive for the presence of an anti-endothelin-antibody, whereas in patients without graft rejection only 6.2% have a detectable anti-endothelin-antibody.

In a preferred embodiment of the invention the determination of presence or absence of an anti-endothelin-receptor antibody is done by detecting one or more of the antibodies selected from the group of IgA-antibody, IgG-antibody and IgM-antibody and more in particular an IgG1, IgG2, IgG3 and IgG4 antibody.

In one embodiment of the invention the invention relates to an immunoassay. There are numerous ways of performing an immunoassay in a preferred embodiment of the invention, the immunoassay is a luciferase assay and/or an ELISA.

The invention further relates to the use of an endothelin-receptor-peptide or a functional analog thereof for the diagnosis of a disease and is selected from the group of graft rejection, pre-enclampsia also referred to as toxemia, hypertension, vasculitis, collagenosis, and inflammatory rheumatic disease and arteriosclerosis.

In a preferred embodiment the endothelin-receptor peptide is an endothelin-receptor-A peptide.

The invention relates to a research and/or diagnostic kit for the diagnosis of a disease selected from the group of diabetes graft rejection, pre-eclampsia also referred to as toxemia, hypertension, vasculitis, collagenosis, an inflammatory rheumatic disease and arteriosclerosis, wherein the kit comprises an endothelin-receptor-peptide or a functional analog thereof.

In a further embodiment the invention relates to the use of an inhibitor of an anti-endothelin-receptor-antibody or an inhibitor of an endothelin-receptor for the production of a medicament, in a preferred embodiment the anti-endothelin-receptor-antibody is an anti-endothelin-receptor-A-antibody or an inhibitor of an endothelin-receptor-A.

DETAILED DESCRIPTION OF THE INVENTION

The inventors have found that the diseases may be diagnosed by detecting the presence or absence of an anti-endothelin-receptor antibody in a sample from a patient to be diagnosed. In fact, the inventors have found that 95% of patients which have a graft rejection are positive for the anti-endothelin-antibody. The same anti-endothelin-antibody may be detected only in 6.2% of the cases in patients with no graft rejection.

Thus, the present invention relates to a method for diagnosis of a disease, wherein presence or absence of an anti-endothelin-receptor antibody is determined in a sample from a patient to be diagnosed.

It has been possible to demonstrate that there is a relationship between the presence of said anti-endothelin-receptor antibody and the likelihood of graft rejection, the disease pre-eclampsia also referred to as toxemia, hypertension, vasculitis, collagenosis, and inflammatory rheumatic disease and arteriosclerosis. In cytobiological and immuno histochemical studies, as well as investigations on biopsy materials, it has been found that there are no addition immunological risk factors to transplant rejection. It has been demonstrated that the presence of the anti-endothelin-receptor antibody gives rise to rejection reactions in a recipient with transplanted organs. Further, it has been demonstrated that the presence of an anti-endothelin-receptor antibody is diagnostic for pre-eclampsia, hypertension, vasculitis, collagenosis and inflammatory rheumatic disease and arteriosclerosis.

In connection with the present invention, a number of general terms will be used as follows: "graft" in the meaning of the invention is an organ or tissue which has been transplanted or is to be transplanted. In the meaning of the invention, however, grafts can also be particular implants comprised of materials or components incorporated in a body for a limited period of time or for life in order to assume specific substitute functions. For example, such grafts can be made of inorganic matter coated with organic substances such as cartilage or bone cells.

According to the invention "graft rejection" is to be understood to be induction of an immune reaction to the graft in the recipient. An immune reaction in the recipient is a specific protective or defense reaction of the body against the antigens of the transplant.

The "endothelin-receptor" may be present in its natural cellular environment and can be used together with the material associated with the receptor in its natural state as well as in isolated form with respect to its primary, secondary and tertiary structures, the endothelin-receptor is well known to those skilled in the art. Based on the weight of the whole receptor in the preparation to be used according to the invention, the isolated receptor should account for at least 0,5%, preferably at least 5% more preferably at least 25%, and in a particular preferred embodiment at least 50%. The receptor is preferably used in isolated form, i.e. essentially free of other proteins, lipids, carbohydrates or other substances naturally associated with the receptor. "Essentially free of" means that the receptor is at least 75%, preferably at least 85%, more preferably at least 95% and especially preferably at least 99% free of other proteins, lipids, carbohydrates or other substances naturally associated with the receptor.

In connection with the present invention, the naturally occurring receptor as well as all modifications, mutants or derivatives of the endothelin-receptor can be used. Similarly, an endothelin-receptor produced by means of recombinant techniques, which receptor includes amino acid modifications, such as inversions, deletions, insertions, additions etc. can be used according to the invention provided that this part of the essential function of the endothelin-receptor is present, namely the capability of binding antibodies. The endothelin-receptor being used may also comprise exceptional amino acids and/or modifications of such as alkylation, oxidation, thiol-modification, denaturation, oligomerization and the like. The receptor can also be synthesized by chemical means. According to the invention the endothelin-receptor particularly can be a protein and/or peptide or a fusion protein, which in addition to other proteins, peptides or fragments thereof, includes the endothelin-receptor as a whole or in part. Using conventional methods, peptides or polypeptides of the endothelin-receptor which have functionally analogs, analogous properties can be determined by those skilled in the art. For example such polypeptides or peptides have 50-60%, 70% or 80%, preferably 90%, more preferably 95%, and most preferably 98% homology to peptides identified as endothelin-receptor, and said homology can be determined, e.g. by means of Smith-Waterman homology search algorithm, using the MPFRCH Programme (Oxford Molecular), for example.

The term "peptide" of an endothelin-receptor used in the present invention, comprises also molecules differing from the original sequence by deletion(s), insertion(s), substitution(s) and/or other modifications well known in the prior art and/or comprising a fragment of the original amino acid molecule, the endothelin-receptor still exhibiting the properties mentioned above. Also included are allele variants and modifications. Methods of producing the above changes in the amino acid sequence are well known to those skilled in the art and have been described in the standard textbooks of molecular biology, e.g. Sambrook et al. Supra. Those skilled in the art will also be able to determine whether an endothelin-receptor, thus, modified still has the properties mentioned above. Possible endothelin-receptor peptides used according to the invention can be, e.g. the five-amino acid sequence (140-KLLAG-144 (SEQ ID NO. 1)) in the B-loop. In the present specification all of the above illustrated modifications of the endothelin-receptor will be referred to as "functionally analogous peptides or proteins" in brief.

"Sample" in the meaning of the invention can be all biological tissues and fluids such as blood, lymph, urine, cerebral fluid. The sample is collected from the patient and subjected to the diagnosis according to the invention.

The "anti-endothelin-receptor antibody" in the meaning of the invention, which is to be detected, binds the endothelin-receptor in a specific fashion. The antibody can also be modified (e.g. oligomeric, reduced, oxidized and labeled antibodies). The term anti-endothelin-receptor antibody as used herein comprises both intact molecules and also anti-endothelin-receptor antibody fragments such as Fab, F(ab')$_2$ and Fv capable of binding specific epitope determinate of the endothelin-receptor. In these fragments the anti-endothelin-receptor antibody(ies) capability of selectively binding its antigen or receptor is retained in part, the fragments being defined as follows: (1) Fab, the fragment which contains a monovalent antigen-binding fragment of an antibody molecule, can be generated by cleavage of a whole antibody using the enzyme papaine, thereby obtaining an intact light chain and part of a heafy chain; (2) the Fab fragment of an antibody molecule can be produced by treatment of a whole antibody with pepsin and subsequent reduction, thereby obtaining an intact light chain and part of a heavy chain, two Fab fragments per antibody molecule are obtained; (3) F(ab')$_2$ the fragment of the antibody which can be obtained by treatment of a whole antibody with the enzyme pepsin without subsequent reduction, F(ab')$_2$ is a dimer comprised of two Fab fragments held together by two disulfate bonds; (4) Fv defined as fragment modified by genetic engineering which includes the variable region of the light chain and the variable region of the heavy chain is expressed in the form of two chains; and (5) single-chain antibody (SCA) defined as a molecule modified by genetic engineering, which includes the variable region of the light chain and the variable region of the heavy chain, linked by a suitable polypeptide linker to perform a genetically fused single-chain molecule.

The term "epitope" as used in the present invention represents any antigen determinant on the endothelin-receptor. Epitope determinance normally consists of chemically active surface groups of molecules such as amino acids or sugar-side chains and normally has specific features of the free dimensional structure as well as specific chart properties.

The anti-endothelin-receptor antibody binds specifically to the endothelin-receptor or in doing so shows specific immuno reactivity when the anti-endothelin-receptor antibody assumes its function in a binding reaction in the presence of a heterogeneous population of endothelin-receptors or fragments thereof, thereby allowing a conclusion whether the endothelin-receptor or another biological structure is present. Under the present conditions of an immunoassay, the above-mentioned anti-endothelin-receptor antibodies will preferably bind to a specific portion of the endothelin-receptor, while no significant binding to other proteins present in the sample will take place.

"Patients" in the meaning of the invention are understood to be all persons, animals, plants or microorganisms, irrespective whether or not they exhibit pathological changes. In the meaning of the invention, any sample collected from cells, tissues, organs, organisms or the like can be a sample of a patient to be diagnosed. In a preferred embodiment the patient according to the invention is a human. In a further preferred embodiment of the invention the patient is a human suspected to have a disease selected from the group of graft rejection, pre-eclampsia also referred to as toxemia, hypertension, vasculitis, collagenosis, an inflammatory rheumatic disease and arteriosclerosis.

An "immune reaction" in the meaning of the invention is a specific interaction between the endothelin-receptor or peptides or proteins of analogous function and anti-endothelin-receptor antibodies. The immune reaction can be detected using various immunoassays.

"immunoassays" in the meaning of the invention are assays utilizing the specific interaction between the endothelin-receptor and peptides or proteins of analogous function and the anti-endothelin-receptor antibodies, in order to detect the presence or determine the concentration of the anti-endothelin-receptor antibodies. For example, a detection in quantification of the anti-endothelin-receptor antibodies can be performed with the aid of said peptides or proteins of analogous function, e.g. by immuno precipitation or immuno blotting.

In a preferred embodiment of the invention, the invention relates to a method for diagnosis of disease, wherein the anti-endothelin-receptor antibody is an anti-endothelin-receptor-A antibody.

Endothelins play an important role in the regulation of the cardiovascular system (Watson, S. et al., Endothelin, the G-protein link receptor facts book, 1994). They are the most potent vasoconstrictors identified, stimulate cardiac contraction, regulate release of vasoactive substances and stimulate nitrogenesis in blood vessels in primary culture. They also stimulate contraction in almost all other smooth muscles (e.g. uterus, bronchius, stomach) and stimulates secretion in several tissues (e.g. kidney, liver and adrenals). Endothelin-receptors have also been found in the brain, e.g. cerebral cortex and cerebellum. Endothelins have been implicated in a variety of pathophysiological conditions associated with stress. The ETB receptors are thought to play a significant role in endothelium-dependent vasodilation and a minor role in vasoconstriction. In CNS the receptor has been found in the cerebral cortex, hippocampus, cerebellum and astrocites. ETB receptors activate the phosphoinositide pathway through a pertussis-toxin-insensitive-G-protein, thus some actions are pertussis-sensitive (Watson et al., 1994). The ETA receptor is the predominant type of the endothelin-receptor. It mediates contraction in blood vessels, bronchius, uterus and heart; it also inhibits aldosteron secretion. The receptors have been identified in glia cells in the CNS. They activate the phosphoinositide pathway through a pertussis-toxine-insensitive-G-protein, probably of the Gq/G11 class (Watson et al., 1994).

Endothelin itself, endothelin-1 (ET-1) is a potent endothelium-derived vasoconstrictor peptide originally isolated from culture media of vascular endothelial cells (EC) (Yanigisawa, M. H. et al., 1988, A novel potent vasoconstrictor peptide produced by vascular endothelial cells, Nature (London) 332:

411-415) subsequent human genomic cDNA cloning revealed three distinct ET isopeptides designated ET-1, ET-2 and ET-3 (Inoue, A. M., et al., 1989, The human endothelin family: three structurally and pharmacologically distinct isopeptides predicted by three separate genes, Proc. Natl. Acad. Sci., USA, 86: 2863-2867), suggesting the existence of receptor subtypes. cDNA cloning of ET-receptors from bovine red lung has revealed at least the above-mentioned two distinct subtypes. The endothelin-A-receptor seems to be selective for ET-1 and ET-2 and the other endothelin-B -receptor seems to be non-isopeptide selective. Both receptor subtypes comprise seven transmembrane domains common to the G-protein-coupled receptors.

According to the invention the disease is selected from the group of graft rejection, pre-eclampsia also referred to as toxemia, hypertension, vasculitis, collagenosis, an inflammatory rheumatic disease and arteriosclerosis.

In a preferred embodiment the diabetes is type I diabetes.

In a preferred embodiment the collagenosis is a diseases selected from the group of Lupus erythematodes disseminatus, systemic sclerosis, eosinophilia infectiosa, polymyositis, dermatomysistis, periarteriitis nodosa, rheumatoid arthritis, Wegener-granulomatose, CREST-syndrome and SHARP-syndrome.

In a very preferred embodiment the collagenosis is a diseases selected from systemic sclerosis and rheumatoid arthritis.

In a preferred embodiment the inflammatory rheumatic disease is selected from the group of rheumatoid arthritis, fibromygalia, lupus erythematodes, polymyaglia rheumatica, progressive systemic sclerosis, Sjögren-syndrome, systemic lupus erythematodes, Raynaud-Syndrom (Morbus Raynaud) and joint inflammation.

In a very preferred embodiment the inflammatory rheumatic disease is selected from systemic sclerosis, Raynaud-Syndrom (Morbus Raynaud) and rheumatoid arthritis.

In a preferred embodiment the hypertension is selected from the group of adrenal hypertension, arterial hypertension, atherosclerotic hypertension, endocrine hypertension, essential hypertension, fixed hypertension, cardiovascular hypertension, malign hypertension, labile hypertension, neurogenic hypertension, paroxysmal hypertension, portal hypertension, pulmonary hypertension, renal hypertension and secondary hypertension.

In a very preferred embodiment the hypertension is selected from malign hypertension.

Further, in preferred embodiment the arteriosclerosis is selected from the group of central arteriosclerosis, coronary arteriosclerosis, cerebral arteriosclerosis such as apoplexy and encephalomalacia, nephrosclerosis such as diabetic nephrosclerosis and juvenile malign nephrosclerosis and Mönckeberg-arteriosclerosis.

In a preferred embodiment of the invention the determination of the presence or the absence of an anti-endothelin-receptor antibody is done by detecting one or more of the antibodies selected from the group of IgA-antibody, IgG-antibody and IgM-antibody.

Human antibodies can be divided into five classes of immunoglobulins. Class A immunoglobulin (IgA) exists in form which is dissolved in blood as well as in secretory variant. IgA comprises two basic classes. Secretory IgA consist of two immunoglobulin basic molecules, together with a J-chain and a secretory component. More, specifically IgA molecules can prevalent in body secretions.

Class IgG immunoglobulins represent the major part among the immunoglobulins. The antibodies of the secondary immune response taking place upon contact of the immune system of a particular antigen largely belong to the IgG class.

In a particularly preferred embodiment of the invention, the anti-endothelin-receptor antibody is selected from the group of IgG1, IgG2, IgG3 and IgG4.

"Immunoassays" in the meaning of the invention are assays utilizing the specific interaction between the endothelin-receptor and peptides or proteins of analogous function and the anti-endothelin-receptor antibody, in order to detect the presence or determine the concentration of the anti-endothelin-receptor antibodies. For example, the detection and quantification of the anti-endothelin-receptor antibody can be performed with the aid of said peptides or proteins an analogous function, e.g. by immunoprecipitation or immunoblotting. For example, immunoassays in the meaning of the invention can be subdivided into the following steps: (1) anti-endothelin-receptor antibody/endothelin-receptor reaction, (2) if required separation of the anti-endothelin-receptor antibody complex from other components of the reaction mixture especially from non-bound anti-endothelin-receptor antibodies an endothelin-receptor and (3) measuring the response. As for the anti-endothelin-receptor antibody/endothelin-receptor reaction various configurations of passable, e.g. (a) precipitation of one reaction with an access of the other or (b) competition between known quantities of anti-endothelin-receptor antibody or endothelin-receptor and the material to be investigated.

For example, an assay for anti-endothelin-receptor antibodies can be performed by a) using access endothelin-receptors/peptides or proteins of analogous function or b) competition between a labeled anti-endothelin-receptor antibody of known amount and non-labeled antibody of unknown amount for a defined quantity of endothelin-receptor or peptides of proteins of analogous function.

The endothelin-receptor can be immobilized on a solid support to allow separation of the anti-endothelin-receptor antibody/endothelin-receptor complex. For example, the solid support material can be nitrocellulose, polyvinylchloride or polystyrene, e.g. the well of a microtiter plate. The immunoassay may take place in a microfluidic environment. To measure the anti-endothelin-receptor antibody/endothelin-receptor interaction, it is possible to use labeled anti-endothelin-receptor antibodies, labeled endothelin-receptors or secondary reagents, for example. The endothelin-receptor can be labeled radioactively or with enzymes or with fluorescent compounds, for example. Irrespective of the label that is used, the response of the anti-endothelin receptor antibody/endothelin-receptor interaction can be enhanced by utilizing the affinity of the proteins avidine or streptavidine for biotin. The immunoassays used according to the invention can be: (1) immunoassays using radioactive label: (a) radioimmunoassay with competitive binding (RIA) and (b) immunoradiometric assay (IRMA); (2) immunoassays using an enzyme label: (a) enzyme immunoassays (EIA) and (b) enzyme-linked immunosorbenassys (ELISA); (3) immunoassays using a combination of radioisotope and enzyme labels (ultrasensitive enzyme radio immunoassay) (USERIA). Further, the immunoassay according to the invention may be a fluorescent immunoassay, a chemiluminescent assay, an agglutination assay, a nephelometric assay, a turbidimetric assay, a Western Blot, a competitive immunoassay, a non-competitive immunoassay, a homogenous immunoassay, a heterogenous immunoassay, a reporter-assay, e.g. a luciferase assay.

In a preferred embodiment of the invention the immunoassay is an ELISA.

The invention also relates to the use of an endothelin-receptor-peptide or a functional analog thereof for the diagnosis of a disease selected of the group of graft rejection, pre-eclampsia also referred to as toxemia, hypertension, vasculitis, collagenosis, an inflammatory rheumatic disease and arteriosclerosis.

In a preferred embodiment the endothelin-receptor peptide is an endothelin-receptor-A-peptide.

Further, in a preferred embodiment in the use according to the invention, the collagenosis is a disease selected from the group of lupus erythematodes disseminatus, systemic sclerosis, eosinophilia infectiosa, polymyositis, dermatomysistis, periarteriitis nodosa, rheumatoid arthritis, Wegener-granulomatose, CREST-syndrome and SHARP-Syndrome. The inflammatory rheumatic disease is selected from the group of rheumatoid arthritis, fibromygalia, lupus erythematodes, polymyaglia rheumatica, progressive systemic sclerosis, Sjögren-syndrome, systemic lupus erythematodes and joint inflammation. The hypertension is selected from the group of adrenal hypertension, arterial hypertension, atherosclerotic hypertension, endocrine hypertension, essential hypertension, fixed hypertension, cardiovascular hypertension, malign hypertension, labile hypertension, neurogenic hypertension, paroxysmal hypertension, portal hypertension, pulmonary hypertension, renal hypertension, and secondary hypertension. The arteriosclerosis is selected from the group of central arteriosclerosis, coronary arteriosclerosis, cerebral arteriosclerosis such as apoplexy and encephalomalacia, nephrosclerosis such as diabetic nephrosclerosis and juvenile malign nephrosclerosis and Mönckenberg-arteriosclerosis.

The invention further relates to a research and/or diagnostic kit for the diagnosis of a disease selected from the group of graft rejection, pre-eclampsia also referred to as toxemia, hypertension, vasculitis, collagenosis, an inflammatory rheumatic disease and arteriosclerosis, wherein the kit comprises an endothelin-receptor peptide or a functional analog thereof.

In a preferred embodiment the research and/or diagnostic kit comprises an endothelin-receptor-A-peptide or a functional analog thereof.

In a preferred embodiment the research and/or diagnostic kit according to the invention is for the diagnosis of diabetes, preferably type I diabetes, a collagenosis disease is selected from the group of lupus erythematodes disseminatus, systemic sclerosis, eosinophilia infectiosa, polymyositis, dermatomysistis, periarteriitis nodosa, rheumatoid arthritis, Wegener-granulomatose, CREST-syndrome and SHARP-syndrome, the inflammatory rheumatic disease is selected form the group of rheumatoid arthritis, fibromygalia, lupus erythematodes, polymyaglia rheumatica, progressive systemic sclerosis, Sjögren-syndrome, systemic lupus erythematodes and joint inflammation, the hypertension is selected from the group of adrenal hypertension, arterial hypertension, atherosclerotic hypertension, endocrine hypertension, essential hypertension, fixed hypertension, cardiovascular hypertension, malign hypertension, labile hypertension, neurogenic hypertension, paroxysmal hypertension, portal hypertension, pulmonary hypertension, renal hypertension, and secondary hypertension, and the arteriosclerosis is selected from the group of arteriosclerosis is selected from the group of central arteriosclerosis, coronary arteriosclerosis, cerebral arteriosclerosis such as apoplexy and encephalomalacia, nephrosclerosis such as diabetic nephrosclerosis and juvenile malign nephrosclerosis and Mönckenberg-arteriosclerosis.

The immunological test kit according to the invention comprises the endothelin-receptor or a functional analog thereof or the endothelin-receptor-A or a functional analog thereof or peptides or proteins of analogous function per se. The test kit of the invention comprises at least one complete endothelin-receptor or functionally analogous peptides or proteins of said receptor, optionally bound to a solid phase. Furthermore, the test kit may also comprise buffers, specific conjugate together with an enzyme, wash solution, substrate solution to detect the immune reaction and/or a quenching solution. Using these substances a person skilled in the art will be able to perform, e.g. an ELISA to detect the anti-endothelin-receptor antibodies. The buffers, specific conjugate plus enzyme, wash solution, substrate solution to detect immune reaction and quenching solution are well known to those skilled in the art. For example, it would be sufficient to have the test comprise a freeze-dried endothelin-receptor or peptides or proteins of endothelin-receptor analogous function and to add the buffers and other solutions immediately prior to testing the biological material. However, it is also possible to provide the test kit with the endothelin-receptor or its functionally analogous peptides of proteins bound to a solid phase. To detect the anti-endothelin-receptor antibodies the specific conjugate, wash solution, substrate solution and quenching solution, which can be components of the test kit, have to be added according to a mode well known to those skilled in the art.

In another advantageous embodiment of the invention, it is envisioned that the test kit is a test strip comprising the endothelin-receptor or its functionally analogous peptides or proteins immobilized on a solid phase. For example, the test strip can be immersed in serum or other patient samples and incubated. Using a specific biochemical reaction on the test strip after formation of the endothelin-receptor/anti-endothelin-recepetor antibody complex, a specific colour reaction can be triggered by means of which the anti-endothelin-receptor antibody can be detected.

The test system of the invention permits quantification of the anti-endothelin-receptor antibodies directly in a sample, e.g. in plasma of patients. The detection method according to the invention is time saving and cost effected. Large amounts of the samples can be tested and, owing to the low amount of the equipment required, routine laboratories can be used.

The invention also relates to an inhibitor of an anti-endothelin-receptor antibody and an inhibitor of an endothelin-receptor for the production of a medicament. In a preferred embodiment the invention relates to the use of an inhibitor of the endothelin-receptor for the production of a medicament, wherein the endothelin-receptor is an endothelin-receptor-A.

The term "inhibitor" refers to an agent that binds to the receptor but does not provoke the normal biological response. For example, an inhibitor may be any molecule which, when bound to an endothelin-receptor, decreases the activity of or reduces the expression levels of the endothelin-receptor In a preferred embodiment the medicament is for the treatment of a disease selected from the group of graft rejection, pre-eclampsia also referred to as toxemia, hypertension, vasculitis, collagenosis, an inflammatory rheumatic disease and arteriosclerosis. In particular preferred embodiment the collagenosis is a disease selected from the group of selected lupus erythematodes disseminatus, systemic sclerosis, eosinophilia infectiosa, polymyositis, dermatomysistis, periarteriitis nodosa, rheumatoid arthritis, Wegener-granulomatose, CREST-syndrome and SHARP-syndrome, the inflammatory rheumatic disease is selected form the group of Raynaud-Syndrom (Morbus Raynaud), rheumatoid arthritis, fibromygalia, lupus erythematodes, polymyaglia rheumatica, progressive systemic sclerosis, Sjögren-syndrome, systemic lupus erythematodes and joint inflammation, the hypertension is selected from the group of adrenal hypertension, arterial hypertension, atherosclerotic hypertension, endocrine hypertension, essential hypertension, fixed hypertension, cardiovascular hypertension, malign hypertension, labile hypertension, neurogenic hypertension, paroxysmal hypertension, portal hypertension, pulmonary hypertension, renal hypertension, and secondary hypertension, and the arteriosclerosis is selected from the group of arteriosclerosis is selected from the group of central arteriosclerosis, coronary arteriosclerosis, cerebral arteriosclerosis such as apoplexy and encephalomalacia, nephrosclerosis such as diabetic nephrosclerosis and juvenile malign nephrosclerosis and Mönckenberg-arteriosclerosis.

In a preferred embodiment the inhibitor of the endothelin-receptor is selected from the group of
(i) bosentan (4-tert-butyl-N-[6-(2-hydroxy-ethoxy)-5-(2-methoxy-phenoxy)-2,2'-bipyrimidin-4-yl]-benzene-sulfonamide),
(ii) BQ788 (N-cis-2,6-dimethylpiperidinocarbonyl-L-.gamma.-methylleucyl-D-1-methoxy-carbonyltryptophanyl-D-norleucine),
(iii) IRL1083,
(iv) RES7011,
(v) RES7013,
(vi) PD142983,
(vii) IRL2500,
(viii) R0468443,
(ix) A192621,
(x) BQ-778 (N-cis-2,6-dimethylpiperidinocarbonyl-L-γ-methylleucyl-D-1-methoxycarbonyl-tryptophanyl-D-norleucine),
(xi) SB209670,
(xii) sitaxsentan,
(xiii) trans, trans2(4-methoxydhenyl)-4-(1-3-benzodiazol-5-yl)-1-(dibutylamino-carbonylmethyl)-pyrrolidine-3-carboxylic acid (ZD4054)
(xiv) SB 209670
(xv) L-754,142
(xvi) IRL-1620
(xvii) BMS-182874
(xviii) an inhibitor of the endothelin converting enzyme (ECE) such as CGS26303 and phosphoramidon,
(xiv) an anti-sense molecule directed against the endothelin-receptor,
(xvv) antibodies against the endothelin-receptor and
(xvvi) a nucleic acid molecule that results in silencing endothelin receptor B activity through, RNAi such as dsRNA.

In a preferred embodiment the inhibitor of the endothelin-receptor is specific for the endothelin-receptor-A in a selective group of sitaxsentan and trans, trans-2(4-methoxydhenyl)-4-(1-3-benzodiazol-5-yl)-1-(dibutylaminocarbonylmethyl)-pyrrolidine-3-carboxylic acid (ZD4054).

The invention also relates to inhibitors of the anti-endothelin-receptor antibody such as antibodies and anti-sense molecules.

The invention also relates to a method for the removal of an anti-endothelin-receptor antibody from isolated blood. According to this method in a first step the presence or absence of an anti-endothelin-receptor antibody is determined in a blood sample from a patient to be diagnosed wherein, the patient is thought to have a disease selected from the group of graft rejection, pre-eclampsia, hypertension, vasculitis, collagenosis, an inflammatory rheumatic disease and arteriosclerosis, and wherein in a second step upon determining the presence of an anti-endothelin-receptor antibody the isolated blood of the patient is subjected to a plasmapheresis. This plasmapheresis is directed at removing the anti-endothelin-receptor antibody from said isolated blood. The method of plasmapheresis is known to one skilled in the art.

The invention also relates to the use of plasmapheresis for the isolation of an anti-endothelin-receptor antibody from blood.

EXAMPLES

Example I

Endothelin-Receptor ELISA

A suitable streptavidine-coated microtiter plate is loaded with the biotinylated peptide encoding the endothelin-receptor. To this end, 100 µl of a solution per well in the microtiter plate is incubated with 5 µg/ml in a suitable dilution buffer. To measure the non-specific binding, wells are also filled with 100 µl of dilution buffer. The dilution buffer may comprise 0.5% bovine serum albumin, 10 mM phosphate buffer (pH 7,4), 140 mM NaCl and 0,05% TWEEN 20.

Subsequent to the time period of reaction, the peptide solution is moved by decanting and each well is washed three times with 250 µl of a suitable wash buffer. A suitable wash buffer may comprise 10 mM phosphate buffer (pH 7,4), 140 mM NaCl and 0,1% TWEEN 20. Thereafter, 100 µl per well of sera are diluted in a dilution buffer and placed on both the peptide-loaded and comparative plates are incubated. Subsequently, the wells are washed as described above.

The bound antibodies are detected using goat-anti-human immunoglobulin G-antibody having peroxidase coupled thereto. To this end, the antibody is diluted in dilution buffer and incubated (100 µl/well), and this is followed by three wash steps (see above).

Following addition of 100 µl over ready-for-use substrate solution (e.g. 3,3,5,5'-tetramethylbenzidine), the colour develops depending on the amount of peroxidase in the well. The substrate reaction is determined by addition of 100 µl of 0,5 M sulfuric acid. The absorption is measured at 450 nm For evaluation the difference between the absorptions of peptide-loaded microtiter plate and comparative plate with no peptide is formed. Samples having higher absorption then the cut-off are positive. The cut-off is calculated from the mean value of the absorption of negative donors plus three times the standard deviation. In general, a cut-off control or a standard dilution series allowing quantification in relative units is co-performed in the test.

Example II

Various patient groups (with positive diagnosis) as well as controls were tested with respect to the presence or absence of the anti-endothelin-receptor antibody. Table I shows the result obtained.

TABLE I

Detection of anti-endothelin-receptor antibody in blood samples of Healthy controls, control diseases, SSc patients, inflammatory disease patients and patients with graft rejections

| Disease | Presence of anti-endothelin-receptor anti-body in % |
|---|---|
| Healthy controls | 2.8 |
| Control diseases | 10.8 |
| SSc | 57.5 |
| Inflammatory disease | 35 |
| Patients with graft rejection | 95 |
| Patients without graft rejection | 6.2 |

Example III

The invention also relates to a method for a removal of anti-endothelin-receptor antibodies from isolated blood, wherein in a first step the presence or absence of an anti-endothelin-receptor antibody is determined in a blood sample from a patient to be diagnosed wherein the patient is thought to have a disease selected from the group of graft rejection, Raynaud-Syndrom (Morbus Raynaud), diabetes, pre-eclampsia, hypertension, vasculitis, collagenosis, an inflammatory rheumatic disease and arteriosclerosis, and wherein, upon determination the presence of an anti-endothelin-receptor antibody the blood of the patient is subjected to a plasmapheresis. Isolated blood from patients thought to have systemic sclerosis were analysed for the presence on an anti-endothelin-receptor antibody. In both patients the presence of an anti-endothelin antibody was conformed. The isolated blood was subjected to plasmapheresis. Thereupon, the isolated blood was resubjected to the patients. The tighter of the antibody dropt significantly below the cut of value which may be determined according to the invention. The synthese of the systemic sclerosis reduced significantly.

Example IV

We analyzed sera of 212 patients with systemic sclerosis, 60 healthy control subjects, 120 rheumatoid arthritis patients and 124 additional control subjects with either morphea or idiopathic pulmonary hypertension for the presence of antibodies directed endothelin-1 type A receptor ($ET_AR$) by a solid phase assay. Individual organ involvement, patient survival and the effect of immunosuppressive or cell therapies were also assessed. Vascular responsiveness to natural receptor ligands, Endothelin-1 was studied ex vivo in pulmonary resistance arteries.

$ET_AR$-AA was detected in 57.5% of the SSc patients, but only in 10.8% subjects with control diseases, respectively, and 2.8% of the normal subjects. Patients $ET_AR$-AA had more severe disease. Positivity for $ET_AR$-AA strongly predicted development of pulmonary arterial hypertension and SSc-related mortality. The antibody levels were not influenced by commonly used immunosuppression or stem-cell transplantation. Stimulation of pulmonary resistance vessels with $ET_AR$-AA ex vivo increased the vasoconstrictive responsiveness towards Endothelin-1 that could be blocked by corresponding receptor antagonists.

Patients and assessment of clinical manifestations

Serum samples were collected in 212 consecutive patients with scleroderma between January 2004 and November 2006. Patients had limited (n=89), diffuse SSc (n=78), or an overlap syndrome (n=45) with other connective tissue diseases as defined by LeRoy et al, and met by American College of Rheumatology criteria for the classification of SSc (21, LeRoy-E C, J. Rheumatol. 1988, Massi). We obtained control sera from 71 healthy subjects and 239 control disease patients including 115 rheumatoid arthritis patients, 33 patients with morphea, 38 with Raynaud's phenomenon (PRP) and 60 patients with idiopathic pulmonary arterial hypertension. The diagnosis in each control group was made according to established criteria for each condition. Written informed consent to use serum samples for research purpose was obtained from each patient.

We also studied 11 random patients with early diffuse systemic sclerosis before initiation of intravenous cyclophosphamide pulse therapy (750 mg/m² per pulse), 3 patients treated with rituximab and recipients of autologous stem cell transplants included in the ASTIS trial (Laar). First samples were obtained before initiation of therapy and up to seven control samples during 24 months follow-up.

A procedure standardized by European Scleroderma Trials and Research group (EUSTAR) was used to collect data on all patients, and the following variables were collected within the first months of follow-up after serum sampling. Skin fibrosis was assessed by at least two independent investigators with the use of modified Rodnan skin score. The haemoglobin level and ESR were derived from blood samples. Serum was analyzed for the presence of anti-centromere antibodies (ACA), antitopoisomerase antibodies (Scl-70), anti-$AT_1R$ and the anti-$ET_AR$-autoantibodies. Lung function was assessed by the predicted forced vital capacity (FVC) and the diffusion capacity adjusted for haemoglobin concentration (DLCO) by a single breath method. Patients with pathologic pulmonary lung function test were examined by a high resolution CT scan; the remaining patients had a chest X-ray. Cardiac involvement was confirmed by a physician if two of the following changes: diastolic dysfunction, ECG changes, decreased ejection fraction, or palpitations were present.

PAH secondary to SSc was suspected in patients with progressive dyspnoea at moderate exercise (NYHA III), >25 mmHg pulmonary artery systolic pressure by echocardiography, >1.4-fold increase of the FVC/DLCOcSB ratio, or signs of right ventricular failure as assessed by echocardiography (e.g. pericardial effusion, increased diameters of the right ventricle). PAH was considered as proven by >25 mmHg mean pulmonary arterial pressure (mPAP) at rest or ≥35 mmHg at exercise in the presence of pulmonary vascular resistance >3 mmHg/L/min and a pulmonary capillary wedge pressure <15 mmHg by right heart catheterizations. Deaths and resuscitations were only included into the study when related to SSc.

Solid Phase Assay

Anti-$AT_1R$ and the anti-$ET_AR$-autoantibodies were measured by a cell-ELISA The test employs membrane extracts of either $AT_1R$ or the $ET_AR$ overexpressing CHO cells serving as a solid phase. The specificity of the anti-$AT_1R$ and the anti-$ET_AR$-ELISA was proven by blocking experiments using membrane extracts from the corresponding cell lines showing a dose-dependent and antigen-restricted decrease in the antibody binding for respective antigens. In contrast, membrane extracts from non-transfected CHO cells had no blocking effect on the $AT_1R$ and the anti-$ET_AR$ antibody binding.

Cut-off and inter-assay variability. Serum specimens were randomly ordered for analysis and assays were performed by personnel who were unaware of the patients' pathology. All tests were conducted in duplicate for both, the anti-$AT_1R$ and the anti-$ET_AR$ antibody.

Statistics

Receiver-operating-characteristic (ROC) curves were plotted for the sensitivity of the $AT_1R$- and $ET_AR$ antibody detection tests against 1 minus the specificity for all diseases studied and respective cut-off values were determined. Continuous data are presented as medians (with ranges). We performed comparisons between groups with use of Mann-Whitney U test for continuous variables. Additionally, hazard ratios were assessed by Kaplan-Meyer analyses for the first manifestation of pulmonary hypertension, digital ulcers, and death or resuscitation during the observation period. Odds ratios and relative risk were calculated to determine associations with individual organ involvements. Small vessel myography data were analyzed by ANOVA. A P value less than 0.05 was considered significant. Results are expressed as means±SEM, n stands for the number of the studied pulmonary artery ring segments.

ET$_A$R Autoantibodies in Different Diseases

Figure 1:
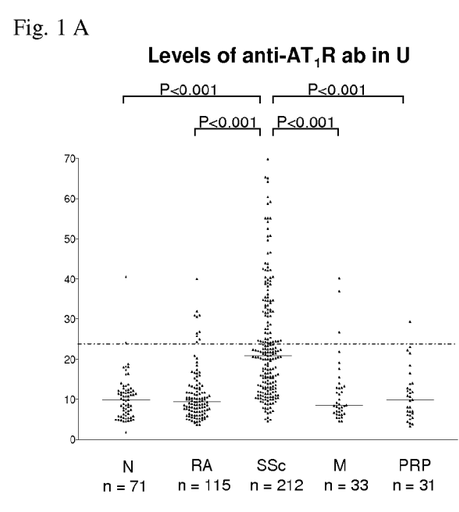
Figure 2:
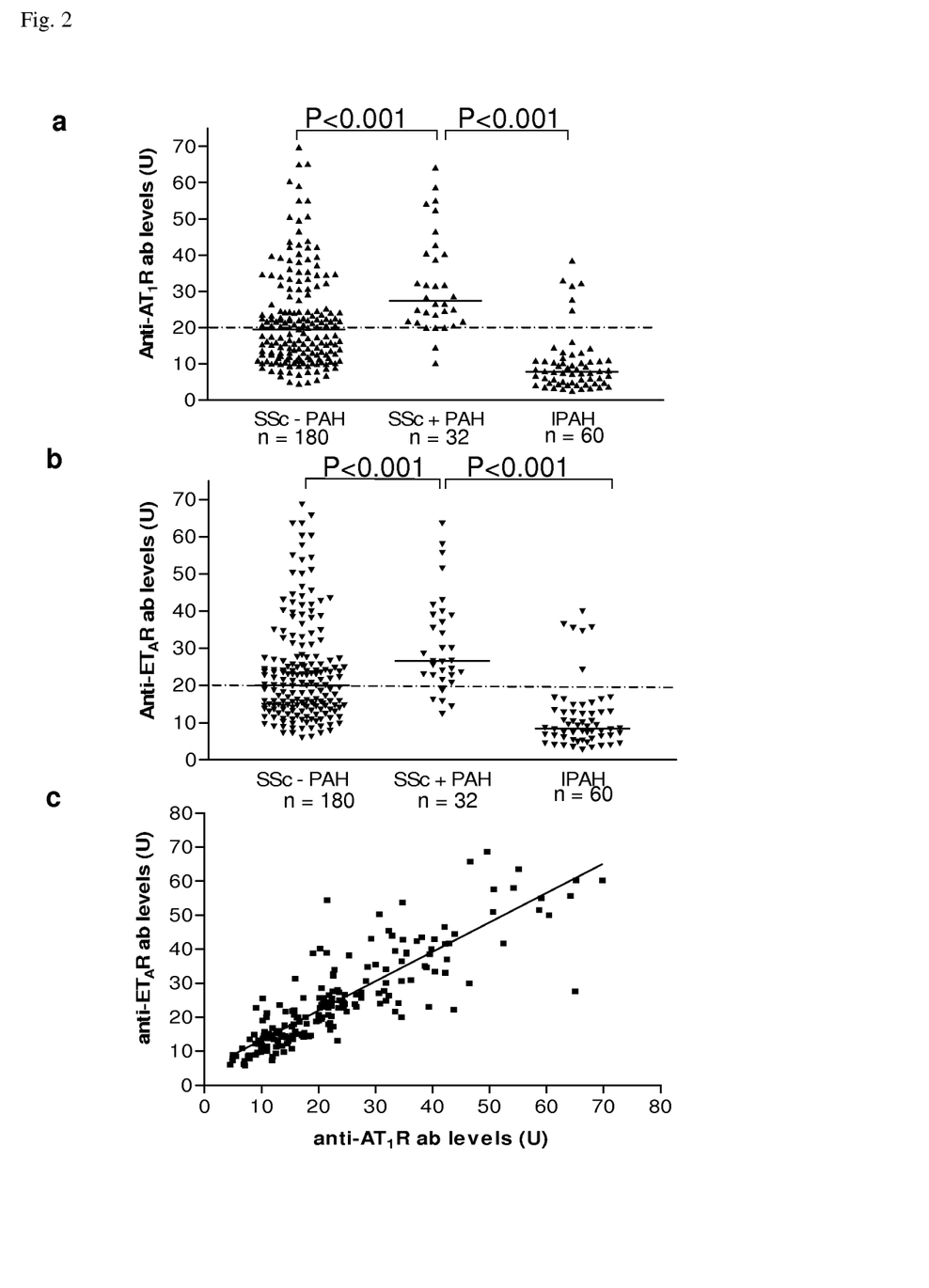
FIG. 2: Comparison of AT$_1$R-(Panel A) and ET$_A$R (Panel B)-autoantibodies levels to each other (Panel C) and in SSc patients with PAH, SSc patients without PAH or patients with IPAH.

ET$_A$R-AA (FIG. 1) were detected in 123 of the 212 SSc (57.5%), but in only 2.8% of the normal subjects, 8.7% of the RA patients and 9.1% of the patients with morphea. The majority of our patients (84%) had both AT$_1$R-AA and ET$_A$R-AA (P<0.001, r$^2$=0.75, FIG. 1, panel B). Singular positivity for AT$_1$R-AA was detected in 6% of SSc patients and in 10% for ET$_A$R-AA only.

Figure 4:
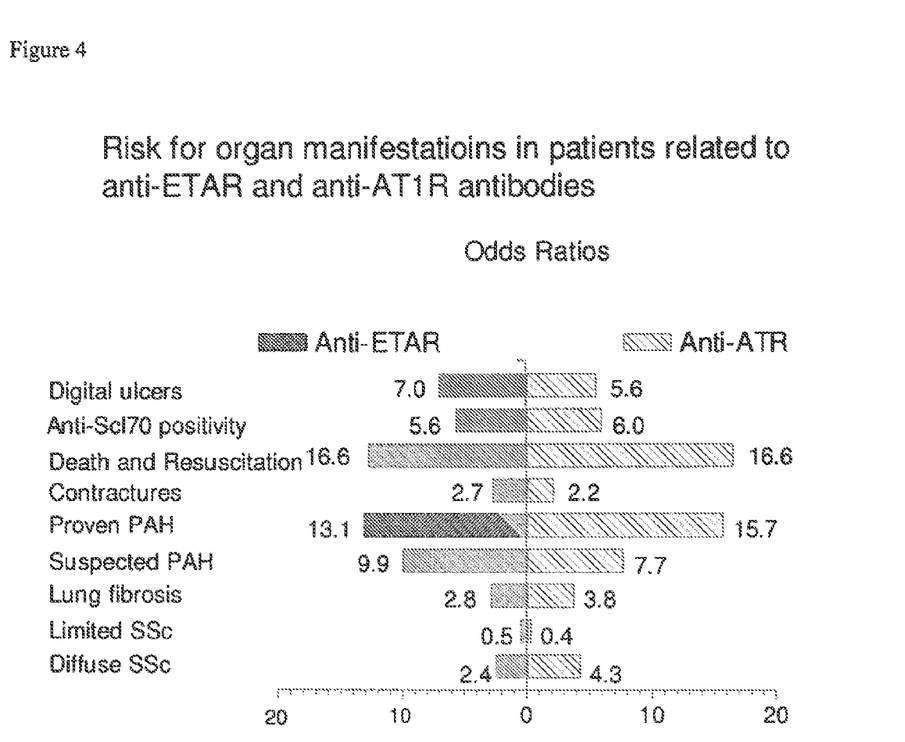
FIG. 4: AT$_1$R-AA and ET$_A$R-AA positivity and disease manifestations determined by clinical and laboratory parameters. Risk for organ manifestations in patients related to anti-ETAR and anti-AT1R antibodies.

The association between anti-receptor antibody positive patients and lung fibrosis was also supported by analyzing lung function parameters. Percentage of predicted FVC and DLCO were lower in the antibody positive patient group when compared to the negatively tested patients. The higher degree of fibrotic changes in the antibody positive cohort was also emphasized by the higher modified Rodnan skin score in the antibody positive group. Patients with anti-receptor antibodies have also a longer disease course and have a higher ESR when compared to the vascular receptor autoantibody negative group (FIG.4).

Predictive Value

Figure 3:
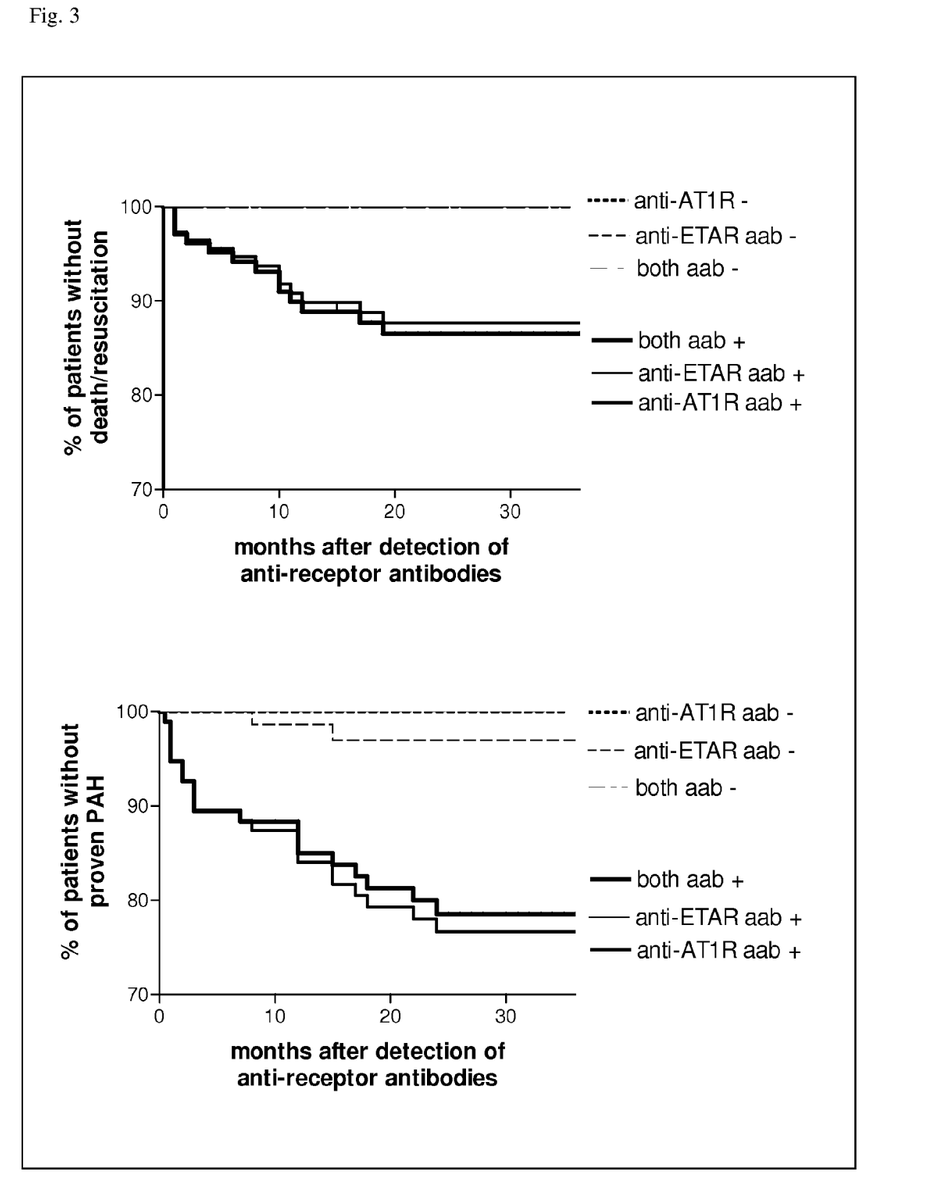
FIG. 3: Kaplan-Meier Curves to analyze the prospective value of anti-AT$_1$R and anti-ET$_A$R antibodies. SSc patients with anti-AT$_1$R, anti-ET$_A$R antibodies, or with both anti-receptor antibodies are at higher risk for SSc-related mortality (panel a) as defined either by death (n=12) or resuscitation (n=3) and are at higher risk for PAH (panel b) during a mean observation period of 22 months. Notice that Y axes start at 70%.

To determine the predictive value of both anti-AT$_1$R and anti-ET$_A$R autoantibodies, we have performed a prospective analysis for SSc-related mortality and PAH after the antibody analysis (FIG. 3). Anti-AT$_1$R antibodies and anti-ET$_A$R antibodies have both a predictive value for mortality (P=0.002 and P=0.001, respectively) during a mean observation period of 22 months. 14 out of the 110 SSc patients with either anti-AT$_1$R or anti-ET$_A$R antibodies died (N=11) or have been resuscitated (N=3), but no single patient in the antibody negative group (P=0.004, FIG. 3a). SSc-related causes of death were multiorgan failure with and without PAH (N=7), PAH (N=3), and cardiac involvement with ventricular tachycardia (N=4).

Furthermore, the anti-receptor antibodies also predict pulmonary arterial hypertension. During the observation period, diagnosis of PAH was made in 21 patients with either anti-AT$_1$R antibodies but not in a single patient without anti-AT$_1$R antibodies (P<0.001, FIG. 4b). Similar results were also obtained for the anti-ET$_A$R antibody positive patients (P<0.001). The two patients negative for anti-ET$_A$R antibodies but developing PAH were positive for the anti-AT$_1$R antibodies and show anti-ET$_A$R antibodies above 16 U. For patients that have both anti-receptor antibodies, the incidence of proven PAH was also increased (P<0.001).

FIGURE CAPTIONS

FIG. 1: Levels and diagnostic value of AT$_1$R-AA and ET$_A$R-AA autoantibodies in different autoimmune pathologies. AT$_1$R-(Panel A) and ET$_A$R-autoantibodies (Panel B) levels measured in serum of healthy control subjects (N), patients with rheumatoid arthritis (RA), systemic sclerosis (SSc), morphea (M), and primary Raynaud's phenomenon (PRP). Median levels are shown as lines; dotted lines represent the upper normal ranges Compared to the antibody levels found in systemic sclerosis, all other diseases revealed lower levels (P<0.001).

The invention claimed is:

1. A method for the diagnosis of a disease comprising, determining the presence of an anti-endothelin-receptor antibody in a blood sample from a patient, by binding the anti-endothelin-receptor antibody to a peptide comprising the sequence KLLAG (SEQ ID NO. 1), wherein the presence of an anti-endothelin-receptor antibody or fragment thereof is indicative of the disease, wherein the disease is selected from the group consisting of systemic sclerosis, morphea, rheumatoid arthritis, pulmonary arterial hypertension, and graft rejection.

2. The method according to claim 1 wherein the anti-endothelin-receptor antibody is an anti-endothelin-receptor-A antibody.

3. The method according to claim 1 wherein the determination of the presence of the anti-endothelin-receptor antibody is by detecting one or more of the antibodies selected from the group consisting of IgA-antibody, IgG-antibody and IgM-antibody.

4. The method according to claim 3 wherein one or more of the antibodies is selected from the group consisting of IgG1, IgG2, IgG3 and IgG4.

5. The method according to claim 1, wherein the presence of the anti-endothelin-receptor antibody in a sample from a patient is determined using an immunoassay selected from the group consisting of immunoprecipitation, enzyme immunoassay (EIA), radioimmunoassay (RIA) or fluorescent immunoassay, a chemiluminescent assay, an ELISA assay, an agglutination assay, nephelometric assay, turbidimetric assay, a Western Blot, a competitive immunoassay, a noncompetitive immunoassay, a homogeneous immunoassay a heterogeneous immunoassay, a bioassay and a reporter assay such as a luciferase assay.

6. The method according to claim 5 wherein the immunoassay is an ELISA.

7. A method for the removal of anti-endothelin-receptor antibodies from isolated blood comprising:
 a) determining the presence of an anti-endothelin-receptor antibody in a blood sample from a patient, wherein the patient is thought to have a disease selected from the group consisting of systemic sclerosis, morphea, rheumatoid arthritis, pulmonary arterial hypertension, and graft rejection; and
 b) removing the anti-endothelin-receptor antibodies from the blood using plasmapheresis.

8. A method for the treatment of a disease selected from the group consisting of systemic sclerosis, morphea, rheumatoid arthritis, pulmonary arterial hypertension, and graft rejection, comprising administering an inhibitor of an anti-endothelin-receptor antibody or an inhibitor of an endothelin-receptor, wherein the inhibitor of the endothelin-receptor is specific for the endothelin-receptor-A and is selected from the group consisting of sitaxsentan and trans, trans-2 (4-methoxydhenyl)-4-(1-3-benzodiazol-5-yl)-1-(dibutylamino-carbonylmethy)-pyrrolidine-3-carboxylic acid (ZD4054).

9. The method of claim 1 wherein the disease is graft rejection.

* * * * *

UNITED STATES PATENT AND TRADEMARK OFFICE
CERTIFICATE OF CORRECTION

PATENT NO. : 8,592,164 B2  
APPLICATION NO. : 12/376200  
DATED : November 26, 2013  
INVENTOR(S) : Schulze-Forster et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 914 days.

Signed and Sealed this
Twenty-first Day of April, 2015

Michelle K. Lee
*Director of the United States Patent and Trademark Office*

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Leu Leu Ala Gly
1               5
```